United States Patent
Chung et al.

(10) Patent No.: US 10,261,181 B2
(45) Date of Patent: Apr. 16, 2019

(54) LASER RADAR SYSTEM CAPABLE OF ACTIVE POLARIZATION

(71) Applicant: NATIONAL CHUNG SHAN INSTITUTE OF SCIENCE AND TECHNOLOGY, Taoyuan (TW)

(72) Inventors: Te-Yuan Chung, Taoyuan (TW); Ruoh-Rou Chang, Taoyuan (TW); Shih-Che Chien, Hsinchu (TW); Yu-Sung Hsiao, Taoyuan (TW)

(73) Assignee: NATIONAL CHUNG SHAN INSTITUTE OF SCIENCE AND TECHNOLOGY (TW)

( * ) Notice: Subject to any disclaimer, the term of this patent is extended or adjusted under 35 U.S.C. 154(b) by 0 days.

(21) Appl. No.: 15/627,935

(22) Filed: Jun. 20, 2017

(65) Prior Publication Data
US 2018/0364354 A1 Dec. 20, 2018

(51) Int. Cl.
*G01S 17/02* (2006.01)
*G01J 4/00* (2006.01)
*G01N 21/21* (2006.01)
*G01S 7/499* (2006.01)

(52) U.S. Cl.
CPC ........... *G01S 17/02* (2013.01); *G01J 4/00* (2013.01); *G01N 21/21* (2013.01); *G01S 7/499* (2013.01)

(58) Field of Classification Search
CPC ............ G01S 7/499; G01S 7/4811; G01N 2021/1793; G01N 21/21–21/23
See application file for complete search history.

(56) References Cited

U.S. PATENT DOCUMENTS

| | | | | |
|---|---|---|---|---|
| 5,126,869 A * | 6/1992 | Lipchak | ............... | G01S 7/4811 349/117 |
| 5,253,033 A * | 10/1993 | Lipchak | ............... | G01S 7/4811 250/203.2 |
| 5,953,110 A * | 9/1999 | Burns | ................... | G01S 7/4816 356/5.01 |
| 7,006,203 B1* | 2/2006 | Book | ....................... | G01C 3/08 356/5.01 |
| 2003/0063884 A1* | 4/2003 | Smith | ..................... | G02B 6/032 385/129 |
| 2010/0006786 A1* | 1/2010 | Babin | ................... | G01F 23/292 250/577 |
| 2011/0051209 A1* | 3/2011 | Yamada | .................... | B60T 7/22 359/197.1 |
| 2011/0051756 A1* | 3/2011 | Morimoto | ............... | G01S 3/783 372/24 |
| 2016/0295178 A1* | 10/2016 | Damberg | ............. | G03H 1/2294 |

* cited by examiner

Primary Examiner — Kara E. Geisel
Assistant Examiner — Violeta A Prieto
(74) Attorney, Agent, or Firm — Schmeiser, Olsen & Watts, LLP

(57) ABSTRACT

A laser radar system capable of active polarization comprises a signal processing unit for sending a control signal; a laser emitting unit for emitting a first laser to a target after receiving the control signal, wherein the laser emitting unit comprises a liquid crystal polarization driver and a liquid crystal polarization component group, and the liquid crystal polarization driver controls a phase delay of the liquid crystal polarization component group to therefore change a polarized state of the first laser; and a laser receiving unit for receiving a second laser reflected off the target and analyzing polarization information of the second laser through the signal processing unit to evaluate surface characteristics of the target.

6 Claims, 4 Drawing Sheets

LASER RADAR SYSTEM CAPABLE OF ACTIVE POLARIZATION

FIELD OF THE INVENTION

The present invention relates to laser radar systems capable of active polarization and, more particularly, to a laser radar system capable of changing the polarized state of a light ray by a liquid crystal polarization component.

BACKGROUND OF THE INVENTION

A conventional laser radar system detects for information, such as information pertaining to time and distance, and evaluates how far a distant object is by time-of-flight (TOF). An advanced conventional laser radar system estimates characteristics of effective reflectance of the surface of a distant object according to the strength of a signal received at a receiving end. A conventional multi-wavelength system further provides relatively limited information pertaining to the spectrum of a distant object; however, the conventional multi-wavelength system gathers limited information required for identifying the distant object, because it cannot directly estimate coarseness and tilt angle of the surface of the object or judge whether the object is artificial, unless by higher spatial resolution, such as joint use of 3D imaging and an intricate algorithm, whereby it can judge by appearance as to whether the object is a vehicle, pedestrian or the like. However, the aforesaid technique not only entails gathering much data but also requires robust computation capability in order to effectuate automated judgment. As a result, the aforesaid judgment can hardly be achieved by a laser radar system with low to medium resolution.

Take a laser radar or laser range finder as an example, the strength of an optical signal provides information pertaining to effective reflectance of an object which a laser beam is reflected off, wherein the effective reflectance depends on the object's surface characteristics, such as coarseness, scattering, and the included angle between the object's surface and incident light. Furthermore, polarization information provides an opportunity to evaluate physical characteristics of the object's surface and even determine whether the object is made of a natural substance or an artificial substance. FIG. 1 shows the contrast between a nearby coarse surface and a highly smooth surface obtained by polarization information.

In general, the light for use in measurement polarization information is usually randomly polarized, and the polarization detection must vary at a detection end, and in consequence a component with a variable polarization direction must be mounted at the front end of a detector as far as flash imaging is concerned. However, the aforesaid technique is likely to mix ambient light and signal light. Furthermore, if a laser radar system uses multiple detectors, a component with a variable polarization direction must be mounted at the front end of each detector, thereby incurring high costs and increasing system complexity.

SUMMARY OF THE INVENTION

In view of the aforesaid drawbacks of the prior art, it is an objective of the present invention to provide a laser radar system capable of active polarization, characterized by an emitting end using a liquid crystal as an optical phase retarder to change the polarized state of a light ray, and a receiving end having one or more receiving ends, so as to dispense with motion components, attain a non-scan low to medium-resolution distance, effectuate polarization information spatial distribution, and reduce the system's manufacturing cost and complexity.

In order to achieve the above and other objectives, the present invention provides a laser radar system capable of active polarization, comprising: a signal processing unit for sending a control signal; a laser emitting unit for emitting a first laser to a target after receiving the control signal, wherein the laser emitting unit comprises a liquid crystal polarization driver and a liquid crystal polarization component group, and the liquid crystal polarization driver controls a phase delay of the liquid crystal polarization component group to therefore change a polarized state of the first laser; and a laser receiving unit for receiving a second laser reflected off the target and analyzing polarization information of the second laser through the signal processing unit to evaluate surface characteristics of the target.

Regarding the laser radar system, the laser emitting unit further comprises: a laser diode; and a laser diode driver for driving the laser diode to send the first laser after receiving the control signal.

Regarding the laser radar system, the liquid crystal polarization component group comprises: a first liquid crystal polarization component disposed at a light-emitting front end of the laser diode; and a second liquid crystal polarization component disposed at a front end of the first liquid crystal polarization component, wherein the liquid crystal polarization driver is electrically connected to the first liquid crystal polarization component and the second liquid crystal polarization component to control the phase delay of the first liquid crystal polarization component and the second liquid crystal polarization component.

Regarding the laser radar system, the laser emitting unit further comprises: a first zoom lens disposed at a front end of the second liquid crystal polarization component so that the first laser falls on the target squarely.

Regarding the laser radar system, the signal processing unit is a digital signal processor (DSP) or a field programmable gate array (FPGA).

Regarding the laser radar system, the laser receiving unit comprises: a second zoom lens for receiving and concentrating the second laser reflected off the target; an optical detector disposed at a rear end of the second zoom lens to detect the second laser and convert the second laser into a current signal; and an amplifier module disposed at a rear end of the optical detector, the amplifier module comprising a pre-amplifying circuit, a filtering and a main amplifying circuit, wherein the pre-amplifying circuit, the filtering and the main amplifying circuit convert the current signal into an amplified voltage signal, filter out noise, and send a second voltage signal to the signal processing unit.

Regarding the laser radar system, the first laser is a single high-power pulse laser.

Regarding the laser radar system, the optical detector is an optoelectronic diode.

Regarding the laser radar system, the laser receiving unit has multiple laser receiving ends.

Therefore, the laser radar system of the present invention is characterized in that the liquid crystal polarization driver and the liquid crystal polarization component group (which comprises one or more liquid crystal polarization components) change the polarized state of a laser source to simplify the judgment of a distant object's characteristics (for example, effectuates judgment of a distant objects, such as vehicles in motion, pedestrians, artificial objects, and natural objects, and provides an opportunity to distinguish a camouflaged object from a natural object) by low to medium resolution and in the situations as follows: introduction of just one or more liquid crystal polarization components and a driving circuit thereof, dispensing with any complicated algorithm or robust computation. Furthermore, the surface of an ice crystal has specific angles which affect the polarized state significantly. If the laser radar system of the present invention is mounted on an aircraft, it can detect the distribution patterns of ice crystals and raindrops in the air and thus give an alert to ice formed on the surface of the fuselage of the aircraft.

BRIEF DESCRIPTION OF THE DRAWINGS

Objectives, features, and advantages of the present invention are hereunder illustrated with specific embodiments in conjunction with the accompanying drawings, in which.

DETAILED DESCRIPTION OF THE PREFERRED EMBODIMENTS

The wording "front end" used hereunder refers to an end positioned proximate to a target. The wording "rear end" used hereunder refers to an end positioned distal to the target.

Figure 1B:
FIG. 1(B) is a picture of an image taken at a polarized angle.
Figure 1A:
FIG. 1(A) is a picture of an image taken by visible light.
Figure 2:
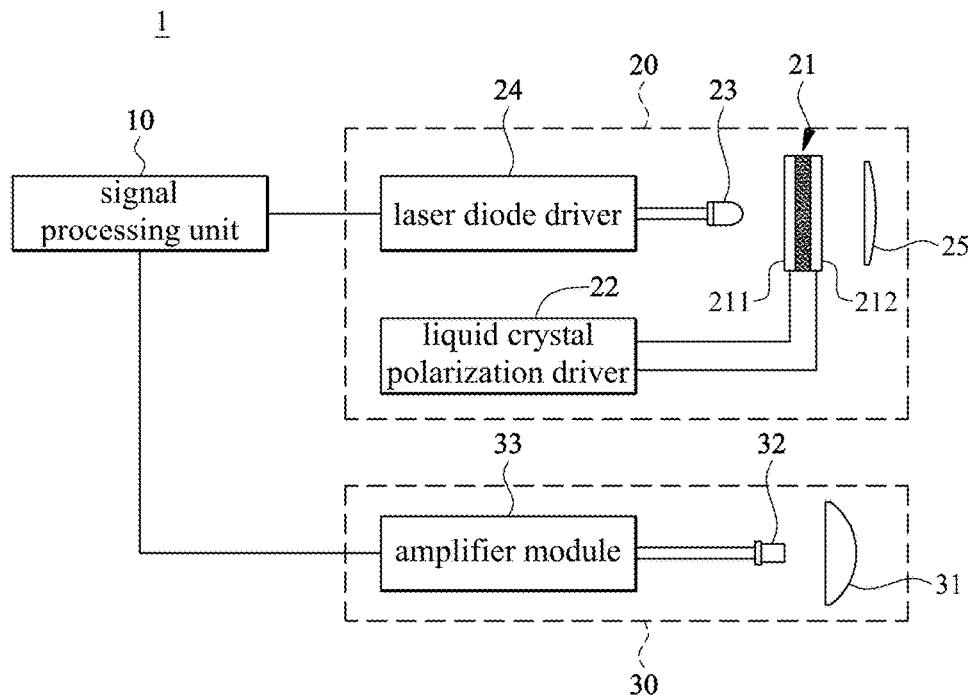
FIG. 2 is a block diagram of a laser radar system capable of active polarization according to an embodiment of the present invention.

Referring to FIG. 1 and FIG. 2, in an embodiment of the present invention, a laser radar system 1 capable of active polarization comprises a signal processing unit 10, a laser emitting unit 20 and a laser receiving unit 30.

The laser emitting unit 20 comprises a liquid crystal polarization component group 21, a liquid crystal polarization driver 22, a laser diode 23, a laser diode driver 24 and a first zoom lens 25.

The signal processing unit 10 is electrically connected to the laser diode driver 24 and sends a control signal to the laser diode driver 24. After receiving the control signal, the laser diode driver 24 drives the laser diode 23 to send a first laser SL1. The first laser SL1 is a single high-power pulse laser.

The liquid crystal polarization component group 21 comprises a first liquid crystal polarization component 211 and a second liquid crystal polarization component 212. The first liquid crystal polarization component 211 is disposed at a light-emitting front end of the laser diode 23. The second liquid crystal polarization component 212 is disposed at a front end of the first liquid crystal polarization component 211. The liquid crystal polarization driver 22 is electrically connected to the first liquid crystal polarization component 211 and the second liquid crystal polarization component 212 to control the phase delay of the first liquid crystal polarization component 211 and the second liquid crystal polarization component 212.

In this embodiment, the liquid crystal polarization component group 21 comprises two liquid crystal polarization components. In a variant embodiment, the liquid crystal polarization component group 21 comprises the liquid crystal polarization components in the other number. Hence, the liquid crystal polarization component group 21 comprises just one liquid crystal polarization component or comprises at least three liquid crystal polarization components.

The first zoom lens 25 is disposed at a front end of the second liquid crystal polarization component 212 so that the first laser SL1 falls on a target squarely. The first zoom lens 25 comprises a collimator.

The laser receiving unit 30 comprises a second zoom lens 31, an optical detector 32 and a amplifier module 33. The second zoom lens 31 receives and concentrates a second laser SL2 reflected off the target. The optical detector 32 is disposed at a rear end of the second zoom lens 31 to detect the second laser SL2 and convert the second laser SL2 into a current signal SI. The optical detector 32 comprises an optoelectronic diode.

In an embodiment of the present invention, the laser receiving unit 30 has one or more laser receiving ends. The laser radar system 1 has a laser emitting end for changing the polarized state of a laser source by the liquid crystal polarization component group 21 rather than a polarization component disposed at the laser receiving end, thereby reducing the system's manufacturing cost. In general, a conventional polarization component is disposed at the laser receiving end according to the prior art; if the laser receiving unit has N laser receiving ends (N>1), N polarization components will be required. By contrast, according to the present invention, the liquid crystal polarization component group 21 is disposed at the laser emitting end; hence, regardless of the number of the laser receiving ends of the laser receiving unit, the required number of the polarization components remains unchanged.

Figure 3:
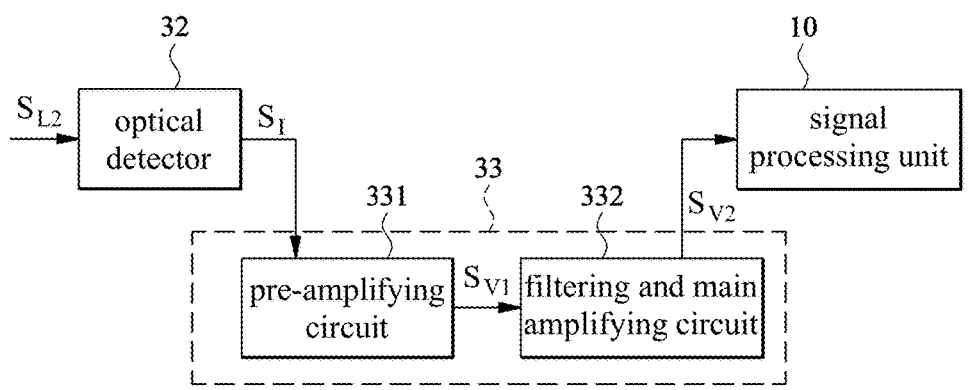
FIG. 3 is a schematic view of optoelectronic conversion effectuated by a laser receiving unit according to an embodiment of the present invention.

Referring to FIG. 3, the amplifier module 33 comprises a pre-amplifying circuit 331, a filtering and a main amplifying circuit 332. The pre-amplifying circuit 331 converts the current signal SI into a first voltage signal SV1. The filtering and the main amplifying circuit 332 amplify the first voltage signal SV1, filter noise, and send a second voltage signal SV2 to the signal processing unit 10.

The signal processing unit 10 analyzes the polarization information of the second laser SL2 and thereby evaluates the target's surface characteristics. The signal processing unit 10 receives the second voltage signal SV2 and performs signal processing. In this embodiment, the signal processing unit 10 is a digital signal processor (DSP) or a field programmable gate array (FPGA).

Semiconductor laser is intrinsically linear polarized light and displays monochromic characteristics; hence, linear polarized light propagating in different directions can be achieved by changing the phase delay with a liquid crystal. On the other hand, a change in the polarized state of the first laser SL1 does not lead to a change in the time signal of time-of-flight (TOF); however, the resultant signal strength varies from polarized state to polarized state. Hence, when it comes to the polarized state and the target's surface characteristics, it is feasible for the signal processing unit 10 to calculate Stokes parameters and Mueller matrix as follows:

$$\vec{S}_{detect} = [M]\vec{S}_{source} \tag{1}$$

equation (1) expresses the relationship between Stokes parameters and Mueller matrix, where $\vec{S}_{source}$ denotes Stokes parameter of a laser source, $\vec{S}_{detect}$ denotes the Stokes parameter of the light signal received by the optical detector, [M] denotes the target's feature Mueller matrix. The calculation involves changing the laser source's polarized state and Stokes parameters and measuring Stokes parameters of the corresponding optical detector to infer matrix parameters in the Mueller matrix of the target, thereby estimating the object's surface characteristics.

In general, four different linear polarized states, namely 0°, 45°, 90° and 135°, are required for a laser source to change its output Stokes parameters, and its Stokes parameters $\vec{S}_{source}$ are as follows:

$$\begin{bmatrix} 1 \\ 1 \\ 0 \\ 0 \end{bmatrix}, \begin{bmatrix} 1 \\ 0 \\ 1 \\ 0 \end{bmatrix}, \begin{bmatrix} 1 \\ -1 \\ 0 \\ 0 \end{bmatrix}, \text{and} \begin{bmatrix} 1 \\ 0 \\ -1 \\ 0 \end{bmatrix}. \quad (2)$$

As for the optical detector, only the parameter $S_0$ is measurable, thereby requiring equation (3).

$$S_{0\_detector} = [1\ 0\ 0\ 0] \cdot R \cdot [M] \vec{S}_{source} \quad (3)$$

In equation (3), R denotes the object's effective reflectance. The Mueller matrix is expressed by equation (4).

$$[M] = \begin{bmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{bmatrix} \quad (4)$$

In equation (4), $M_{11}$ is defined as 1. Mueller matrix is a diagonal symmetric matrix; hence, $M_{ij}=M_{ji}$, and it has only nine variables. The calculating involves changing the laser source's Stokes parameters and measuring effective reflectance R and essential elements of the Mueller matrix of the object with respect to $S_{0\_detector}$. Take $S_{source\_0°}$ and $S_{source\_90°}$ as an example, values measured by the optical detector are expressed by equation (5) and equation (6).

$$S_{0\_detector\_0°} = R \cdot (1 + M_{12}) \quad (5)$$

$$S_{0\_detector\_90°} = R \cdot (1 - M_{12}) \quad (6)$$

Therefore, the object's effective reflectance R and $M_{12}$ can be calculated easily, so are the other parameters. Given the resultant elements of the Mueller matrix, it is feasible to calculate the object's coarseness as disclosed in citation 1. The polarized angle is calculated by a linear polarized object's Mueller matrix (equation (7)):

$$\frac{1}{2}\begin{bmatrix} 1 & \cos 2\theta & \sin 2\theta & 0 \\ \cos 2\theta & \cos^2 2\theta & \sin 2\theta \cdot \cos 2\theta & 0 \\ \sin 2\theta & \sin 2\theta \cdot \cos 2\theta & \sin^2 2\theta & 0 \\ 0 & 0 & 0 & 0 \end{bmatrix} \quad (7)$$

By equation (7), it is feasible to calculate the included angle between the object's surface and the laser emitting end. Afterward, referring to FIG. 4, the object's surface-to-air refractive index is estimated by the Fresnel equation.

Figure 4:
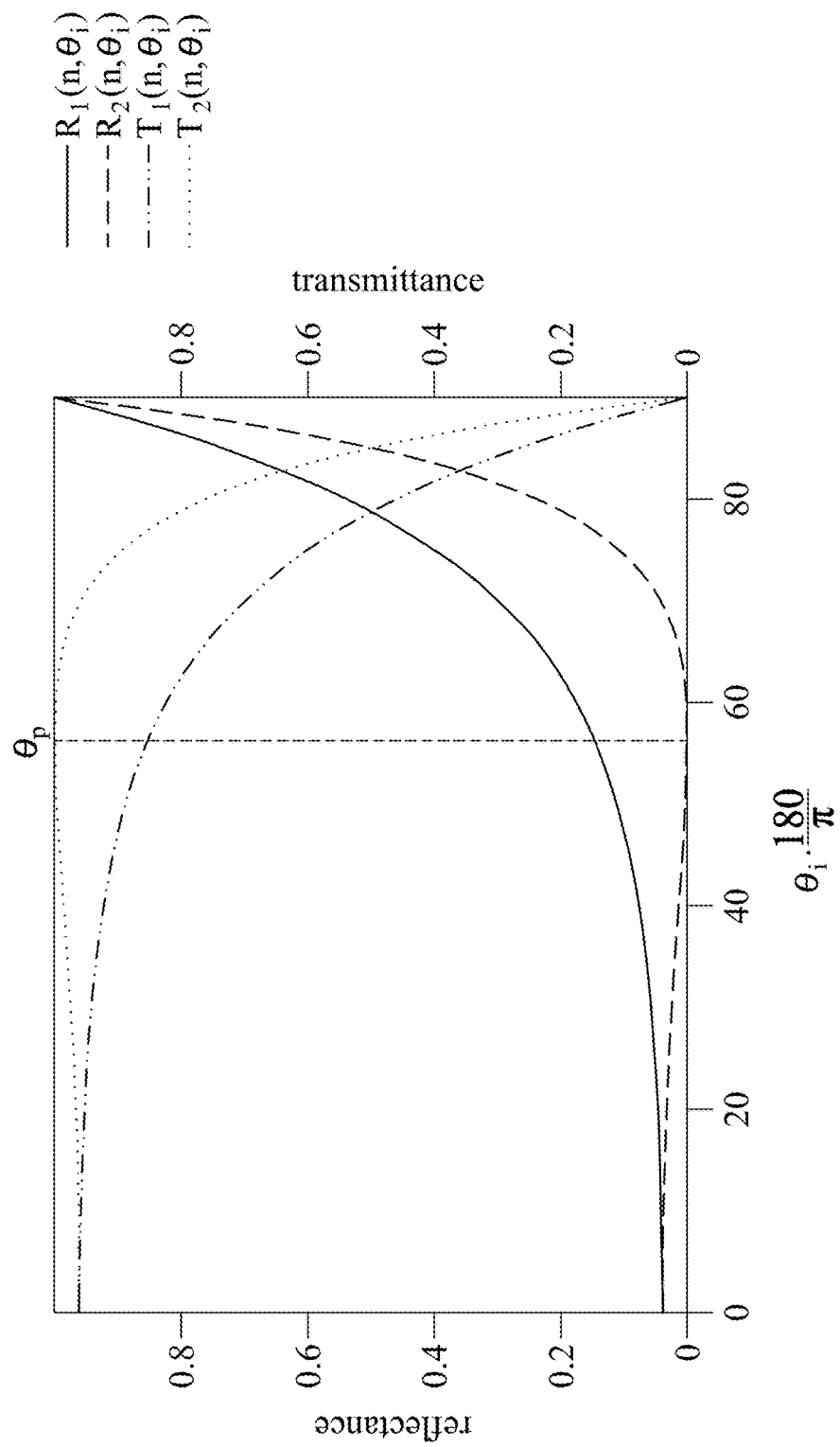
FIG. 4 shows graphs of reflectance and transmittance attributed to TE polarized wave and TM polarized wave and calculated by the Fresnel equation against angle of incidence according to an embodiment of the present invention.

FIG. 4 shows graphs of reflectance and transmittance attributed to TE polarized wave and TM polarized wave and calculated by the Fresnel equation against angle of incidence $$\left(\theta_i \cdot \frac{180}{\pi}\right)$$

according to an embodiment of the present invention, where $\theta_i$ denotes angle of incidence (curvature), $\theta_p$ denotes Brewster's angle, $R_1(n, \theta_i)$ denotes an increase in reflectance of TE polarized wave as a result of an increase in angle of incidence, $R_2(n, \theta_i)$ denotes an increase in reflectance of TM polarized wave as a result of an increase in angle of incidence, $T_1(n, \theta_i)$ denotes an increase in transmittance of TE polarized wave as a result of an increase in angle of incidence, and $T_2(n, \theta_i)$ denotes an increase in transmittance of TM polarized wave as a result of an increase in angle of incidence.

Figure 5:
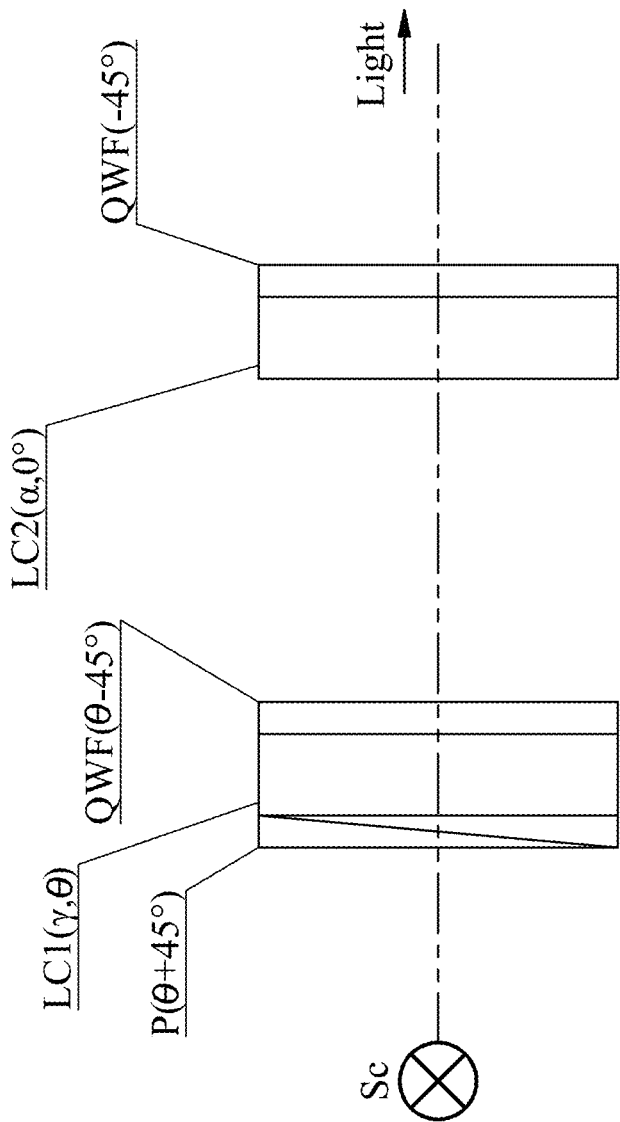
FIG. 5 (PRIOR ART) is a schematic view of a completely polarized state generator which has a fixed polarizer and two liquid crystal phase variable retarders according to citation 2.

Therefore, the laser radar system of the present invention generates detailed information about a distant object by polarization measurement and thus has a higher chance of determining the attributes of the distant object, such as coarseness, scattering, the included angle between the object's surface and incident light, and whether the object is made of a natural substance or an artificial substance. Regarding generation of various polarized states by a liquid crystal, citation 2 proposes using two liquid crystal components to achieve any polarized state as needed and thereby effectuate generation of various polarized states. Referring to FIG. 5, it is a schematic view of a completely polarized state generator which has a fixed polarizer and two liquid crystal phase variable retarders according to citation 2, wherein the monochromic source is denoted by Sc, fixed linear polarizer by P, first liquid crystal phase variable detarder by LC1, second liquid crystal phase variable detarder by LC2, and quarter-wave plate by QWF, with the X-axis corresponding to the slow axis of LC2, allowing an angle to be formed between the slow axis of LC1 and the X-axis. A phase shift and a phase shift are introduced into LC1 and LC2, respectively. The major axes of QWF and P are parallel and have an orientation angle of −45° relative to the slow axis of LC1.

Citation 1: W. Yang, G. H. Gu, X. J. Zhou, F. Y. Xu, and K Ren, "The estimation of surface roughness with the utilization of Mueller matrix," *Infrared Physics & Technology*, vol. 76, pp. 748-755, May 2016.

Citation 2: M. Shribak, "Complete polarized state generator with one variable retarder and its application for fast and sensitive measuring of two-dimensional birefringence distribution," *Journal of the Optical Society of America*, vol. 28, p. 9, 2011.

Therefore, the present invention provides a laser radar system capable of active polarization to gather surface information of a distant object by changing the polarized state of a laser emitting end, determine attributes and features of the object by a relatively level of computation, apply to judgment of objects, such as vehicles in motion, pedestrians, rails, or even military camouflage, and natural objects. Hence, the present invention is applicable to a detection system for smart vehicles as well as military range finding and identification. Furthermore, with polarization signals being capable of discerning the difference between an ice crystal and a droplet in the air, ice formed on the fuselage of an aircraft can be detected by the laser radar system of the present invention, if the laser radar system is mounted on the aircraft.

The present invention is disclosed above by preferred embodiments. However, persons skilled in the art should understand that the preferred embodiments are illustrative of the present invention only, but should not be interpreted as restrictive of the scope of the present invention. Hence, all equivalent modifications and replacements made to the aforesaid embodiments should fall within the scope of the present invention. Accordingly, the legal protection for the present invention should be defined by the appended claims.

What is claimed is:

1. A laser radar system capable of active polarization, comprising:
    a signal processing unit for sending a control signal;
    a laser emitting unit, electrically coupled to the signal processing unit, for emitting a first laser to a target after receiving the control signal, wherein the laser emitting unit comprises a liquid crystal polarization driver and a liquid crystal polarization component group, and the liquid crystal polarization driver controls a phase delay of the liquid crystal polarization component group to therefore change a polarized state of the first laser; and
    a laser receiving unit, electrically coupled to the signal processing unit, for receiving a second laser that is reflected off the target without passing through the liquid crystal polarization component group of the laser emitting unit, wherein the polarized state of the first laser is changed according to a plurality of different states and polarization information of the corresponding second laser is analyzed through the signal processing unit to evaluate surface characteristics of the target;
    wherein the laser radar system includes the laser emitting unit and the laser receiving unit so as to dispense with motion components;
    wherein the laser emitting unit further comprises:
    a laser diode;
    a laser diode driver, electrically coupled to the laser diode and the signal processing unit, for driving the laser diode to send the first laser after receiving the control signal; and
    a first zoom lens;
    wherein the liquid crystal polarization component group comprises:
    a first liquid crystal polarization component disposed at a light-emitting front end of the laser diode; and
    a second liquid crystal polarization component disposed at a front end of the first liquid crystal polarization component, wherein the liquid crystal polarization driver is electrically connected to the first liquid crystal polarization component and the second liquid crystal polarization component to control a phase delay of the first liquid crystal polarization component and the second liquid crystal polarization component;
    wherein the first zoom lens is disposed at a front end of the second liquid crystal polarization component so that the first laser falls on the target squarely.

2. The laser radar system of claim 1, wherein the laser receiving unit further comprises:
    a second zoom lens for receiving and concentrating the second laser reflected off the target;
    an optical detector disposed at a rear end of the second zoom lens to detect the second laser and convert the second laser into a current signal; and
    an amplifier module disposed at a rear end of the optical detector, the amplifier module comprising a pre-amplifying circuit, a filtering and a main amplifying circuit, wherein the pre-amplifying circuit, the filtering and the main amplifying circuit convert the current signal into an amplified voltage signal, filter out noise, and send a second voltage signal to the signal processing unit.

3. The laser radar system of claim 2, wherein the optical detector is an optoelectronic diode.

4. The laser radar system of claim 1, wherein the signal processing unit is one of a digital signal processor (DSP) and a field programmable gate array (FPGA).

5. The laser radar system of claim 1, wherein the first laser is a single high-power pulse laser.

6. The laser radar system of claim 1, wherein the signal processing unit analyzes the polarization information of the second laser to evaluate surface characteristics of the target, based on changing the polarized state and Stokes parameters of the first laser according to the plurality of different states and measuring Stokes parameters of the corresponding second laser to infer matrix parameters in an Mueller matrix of the target.

* * * * *